United States Patent [19]

Spears

[11] Patent Number: 5,092,841
[45] Date of Patent: Mar. 3, 1992

[54] METHOD FOR TREATING AN ARTERIAL WALL INJURED DURING ANGIOPLASTY

[75] Inventor: James R. Spears, Bloomfield Hills, Mich.

[73] Assignee: Wayne State University, Detroit, Mich.

[21] Appl. No.: 525,104

[22] Filed: May 17, 1990

[51] Int. Cl.$^5$ ............................................ A61M 29/00
[52] U.S. Cl. ...................................... 604/96; 606/194; 128/400; 128/401; 600/36; 623/1; 623/12; 604/113
[58] Field of Search ............................. 604/96, 101, 113; 606/7, 8, 13–15, 192–195; 600/36; 623/1, 12; 128/395, 397, 398, 399–401

[56] References Cited

U.S. PATENT DOCUMENTS

| 3,975,350 | 8/1976 | Hudgin et al. | 623/1 |
| 3,988,782 | 11/1976 | Dordik et al. | 600/36 |
| 4,378,017 | 3/1983 | Kosugi et al. | 424/35 |
| 4,713,402 | 12/1987 | Solomon | 604/96 |
| 4,749,585 | 6/1988 | Greco et al. | 623/1 |
| 4,754,752 | 7/1988 | Ginsburg et al. | 604/113 |
| 4,776,836 | 10/1988 | Stanley | 604/113 |
| 4,799,479 | 1/1989 | Spears | 606/7 |
| 4,824,436 | 4/1989 | Wolinsky | 604/101 |
| 4,854,320 | 8/1989 | Dew et al. | 128/397 |
| 4,879,135 | 11/1989 | Greco et al. | 623/12 |
| 4,902,290 | 2/1990 | Fleckenstein et al. | 623/1 |
| 4,941,870 | 7/1990 | Okada et al. | 600/36 |
| 4,969,890 | 11/1990 | Sugita et al. | 623/1 |
| 4,994,033 | 2/1991 | Shockey et al. | 604/96 |

FOREIGN PATENT DOCUMENTS

| 8912478 | 6/1989 | Fed. Rep. of Germany . | |
| 0092414 | 10/1983 | Japan | 600/36 |

Primary Examiner—John D. Yasko
Assistant Examiner—Chalin Smith
Attorney, Agent, or Firm—Brooks & Kushman

[57] ABSTRACT

A method for treating a lesion in an arterial wall having plaque thereon and a luminal surface, the arterial wall having been mechanically injured during an angioplasty procedure, the arterial wall and the plaque including fissures resulting therefrom, the method comprising the steps of positioning an angioplasty catheter adjacent to the lesion being treated; delivering a bioprotective material between the arterial wall and the angioplasty catheter so that the bioprotective material is entrapped therebetween and permeates into the fissures and small vessels of the arterial wall during apposition of the angioplasty catheter to the arterial wall; applying thermal energy to the lesion, thereby bonding the bioprotective material to the arterial wall and within the fissures; and removing the angioplasty catheter, the bioprotective material remaining adherent to the arterial wall and within the fissures, thereby coating the luminal surface of the arterial wall with an insoluble layer of the bioprotective material so that the insoluble layer provides at least semi-permanent protection to the arterial wall, despite contact with blood flowing adjacent thereto.

62 Claims, 2 Drawing Sheets

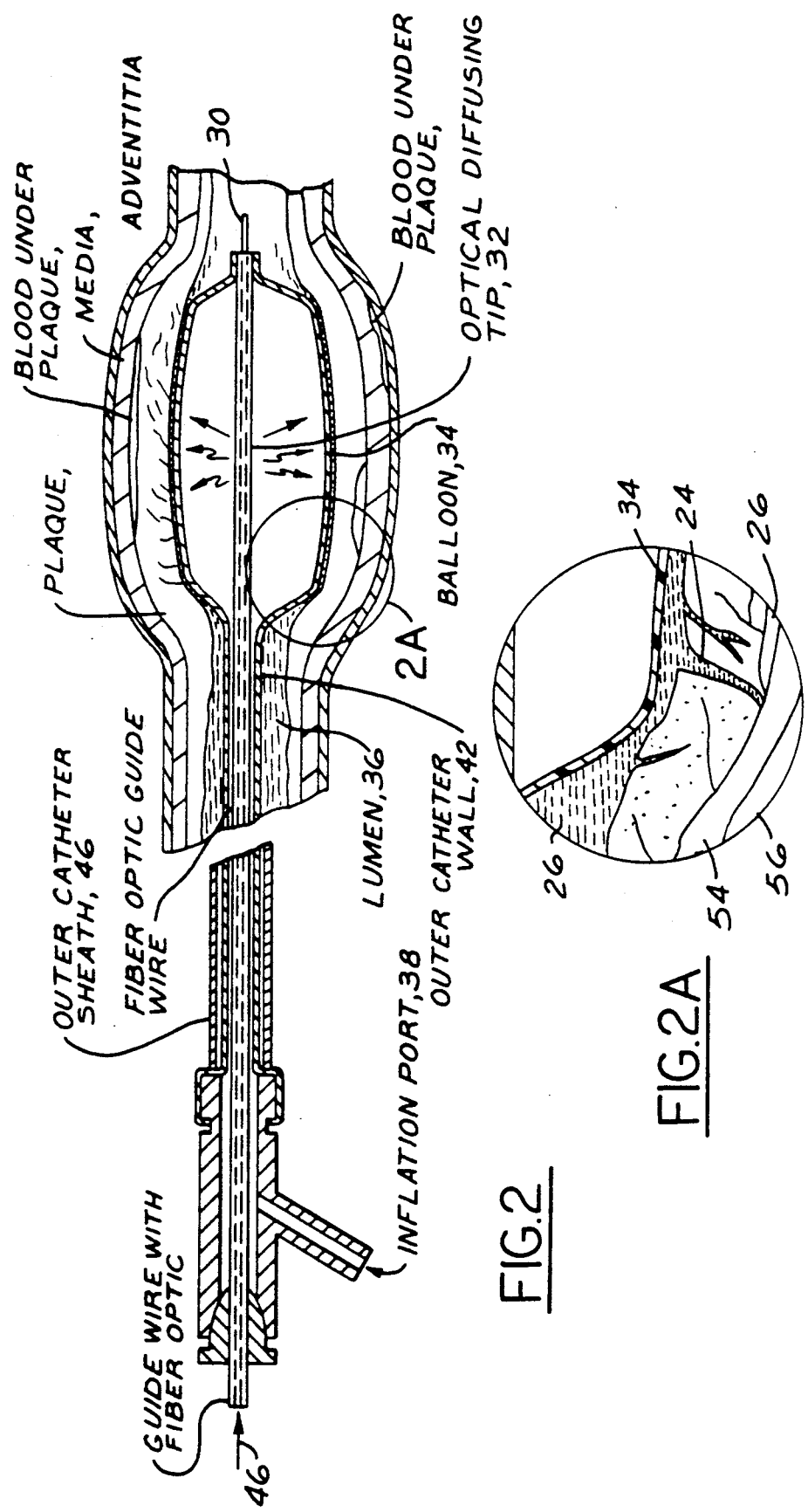

METHOD FOR TREATING AN ARTERIAL WALL INJURED DURING ANGIOPLASTY

STATEMENT OF FEDERALLY SPONSORED RESEARCH

The funding for work described herein was provided in part by the Federal Government, under a grant from the National Institute of Health. The government may have certain rights in this invention.

TECHNICAL FIELD

This invention relates to angioplasty, and more particularly to a method for treating an arterial wall injured during angioplasty.

BACKGROUND ART

Atherosclerosis is a progressive disease wherein fatty, fibrous, calcific, or thrombotic deposits produce atheromatous plaques, within and beneath the intima which is the innermost layer of arteries. Atherosclerosis tends to involve large and medium sized arteries. The most commonly affected are the aorta, iliac, femoral, coronary, and cerebral arteries. Clinical symptoms occur because the mass of the atherosclerotic plaque reduces blood flow through the afflicted artery, thereby compromising tissue or organ function distal to it.

The mortality and morbidity from ischemic heart disease results primarily from atheromatous narrowings of the coronary arteries. Although various medical and surgical therapies may improve the quality of life for most patients with coronary atherosclerosis, such therapies do not favorably change the underlying anatomy responsible for the coronary luminal narrowings. Until recently, there has not been a non-surgical means for improving the perfusion of blood through the lumina of coronary arteries compromised by atheromatous plaque.

Percutaneous transluminal coronary angioplasty has been developed as an alternative, non-surgical method for treatment of coronary atherosclerosis. During cardiac catheterization, an inflatable balloon is inserted in a coronary artery in the region of coronary narrowing. Inflation of the balloon for 15-30 seconds results in an expansion of the narrowed lumen or passageway. Because residual narrowing is usually present after the first balloon inflation, multiple or prolonged inflations are routinely performed to reduce the severity of the residual stenosis or tube narrowing. Despite multiple or prolonged inflations, a mild to moderately severe stenosis usually is present, even after the procedure is otherwise performed successfully.

The physician will often prefer not to dilate lesions that are not severe because there is a good chance that they will recur. Because the occlusion recurs frequently, conventional angioplasty is often considered to be a suboptimal procedure. As a result, it is sometimes attempted only when a patient does not wish to undergo major cardiac surgery.

There are several reasons why the lesions reappear. One is that small clots form on the arterial wall. Tears in the wall expose blood to foreign material and proteins, such as collagen, which are highly thrombogenic. Resulting clots can grow gradually, or can contain growth hormones which are released by platelets within the clot. Additionally, growth hormones released by other cells, such as macrophages, can cause smooth muscle cells and fibroblasts in the region to multiply. Further, there is often a complete loss of the normal single layer of cells constituting the endothelial lining following angioplasty. This layer normally covers the internal surface of all vessels, rendering that surface compatible, i.e. non-thrombogenic and non-reactive with blood. Mechanically, when an angioplasty balloon is inflated, the endothelial cells are torn away. Combination of the loss of the endothelial layer and tearing within the wall often generates a surface which is quite thrombogenic.

Prior art angioplasty procedures also produce injuries in the arterial wall which become associated with inflammation. White cells will migrate to the area and will lay down scar tissue. Any kind of inflammatory response may cause the growth of new tissue. Restenosis or recurrence of the obstruction results because the smooth muscle cells which normally reside within the arterial wall proliferate. Such cells migrate to the area of the injury and multiply in response thereto.

It therefore appears that in order to combat problems associated with cumulating plaque, attention must be paid to: (1) the importance of thrombus; (2) inflammatory changes; and (3) proliferation. Any combination of these factors probably accounts for most cases of restenosis.

In order to address such problems, the cardiology community needs to administer drugs which are biocompatible and not induce toxic reactions. Therefore, it would be helpful to invoke a technique which allows localized administration of drugs that counteract clotting, interfere with inflammatory responses, and block proliferative responses. However, many such drugs when administered are toxic and are associated with potentially serious side effects which make the treatment and prevention of restenosis impractical. Accordingly, even though there is a number of potentially useful drugs, there is a tendency to avoid using them.

One of the other major problems with conventional methods of treatment is that the injured arterial wall exhibits a reduced hemocompatability compared to that associated with a normal arterial wall. Adverse responses which are associated with reduced hemocompatability include platelet adhesion, aggregation, and activation; potential initiation of the coagulation cascade and thrombosis; inflammatory cell reactions, such as adhesion and activation of monocytes or macrophages; and the infiltration of leukocytes into the arterial wall. Additionally, cellular proliferation results in the release of a variety of growth factors. Restenosis probably results from one or a combination of such responses.

Methods for treating atherosclerosis are disclosed in my U.S. Pat. No. 4,512,762 which issued on Apr. 23, 1985, and which is herein incorporated by reference. This patent discloses a method of injecting a hematoporphyrin into a mammal for selective uptake into the atheromatous plaque, and delivering light to the diseased vessel so that the light activates the hematoporphyrin for lysis of the plaque. However, one of the major problems with such treatments is that a flap of material occasionally is formed during the treatment which, after withdrawal of the instrumentation, falls back into the artery, thereby causing abrupt reclosure. This may necessitate emergency coronary artery bypass surgery. Accordingly, such techniques often provide only a temporary treatment for symptoms associated with arterial atherosclerosis.

My U.S. Pat. No. 4,799,479 was issued on Jan. 24, 1989 and is also herein incorporated by reference. This patent discloses a method used in percutaneous transluminal coronary angioplasty wherein a balloon is heated upon inflation. Disrupted tissues of plaque in the arterial wall are heated in order to fuse together fragmented segments of tissue and to coagulate blood trapped with dissected planes of tissues and within fissures created by the fracture. Upon subsequent balloon deflation, a smooth cylindrically shaped channel results.

Approaches such as those disclosed in U.S. Pat. Nos. 4,512,762 and 4,799,479, however, are directed mainly to producing an enhanced luminal result wherein a smooth luminal wall is produced. Problems of biocompatability, including thrombosis, and proliferation of cells tend to remain. Accordingly, the need has arisen to enable a physician to treat patients having atherosclerosis so that the problems of reduced hemocompatability and restenosis are avoided.

As a result of problems remaining unsolved by prior art approaches, there has been a growing disappointment in the cardiology community that until now, no new technology or procedure has been available to dramatically reduce the rate of restenosis.

SUMMARY OF THE INVENTION

The present invention solves the above and other problems by providing a method for treating an arterial wall which has been injured during an angioplasty procedure. The method comprises the steps of positioning an angioplasty catheter adjacent to a lesion to be treated. A bioprotective material is delivered between the arterial wall and the angioplasty catheter so that the bioprotective material is entrapped therebetween and permeates into fissures in the arterial wall during apposition thereto of the angioplasty catheter. To bond the bioprotective material to the arterial wall and within the tissues, thermal energy is applied to the lesion. After removal of the angioplasty catheter, the bioprotective material remains adherent to the arterial wall and within the tissues, thereby coating the luminal surface of the arterial wall with an insoluble layer of the bioprotective material so that the insoluble layer provides at least semi-permanent protection to the arterial wall, despite contact with blood flowing adjacent thereto.

The objects, features, and advantages of the present invention are readily apparent from the following detailed description of the best modes for carrying out the invention when taken in connection with the accompanying drawings.

BRIEF DESCRIPTION OF DRAWINGS

FIG. 2 is a cross-sectional view of one embodiment of the anatomical environment and apparatus used to practice the subject invention, in which the area immediately surrounding the inflated balloon is permeated by the bioprotective material and bonded by thermal energy delivered to the bioprotective material within the arterial wall being treated;

FIG. 2A is an enlarged portion of the circled area depicted in FIG. 2; and

BEST MODES FOR CARRYING OUT THE INVENTION

Figure 1A:
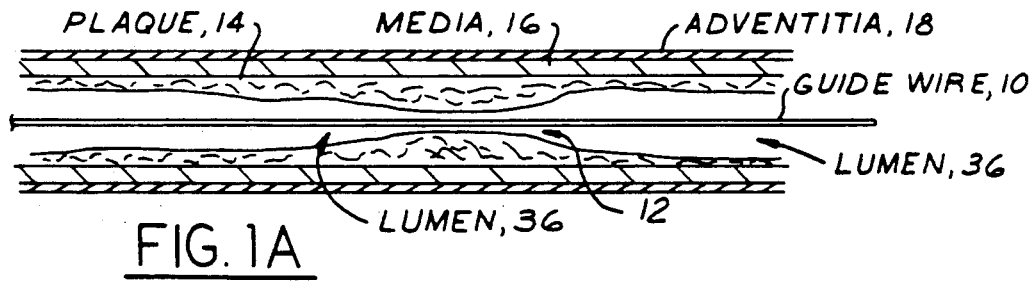
FIG. 1A is a cross-sectional view of a lesion to be treated by a percutaneous transluminal angioplasty procedure, in which plaque is formed within an artery.

FIG. 1A shows a guide wire 10 which is inserted along an artery and through a region 12 which is occluded primarily by plaque 14. Surrounding the plaque 14 are media 60 and adventitia 18. As is now known, the plaque 14 forms an occlusion. The guide wire 10 is usually a stainless steel wire having tightly coiled, but flexible springs. Conventionally, the catheter 20 is made of a plastic, or an elastomeric material and is disposed around the guide wire 10. Following conventional angioplasty, and before applying bioprotective material 26, the balloon section 22 is maneuvered so as to lie adjacent to the plaque 14.

Figure 1B:
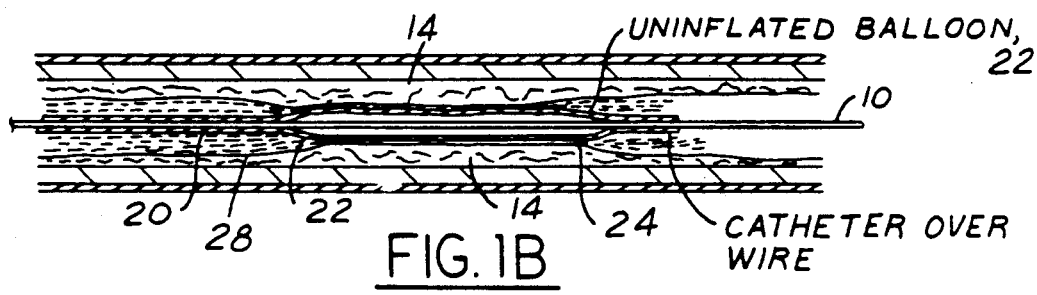
FIG. 1B is a cross-sectional view of the procedure disclosed by the present invention, in which a bioprotective material is delivered to a lesion during distention of an uninflated balloon.

FIG. 1B illustrates the positioning of the uninflated balloon 22 after conventional angioplasty has been performed. Expansion of the balloon 22 to position 22' (FIG. 1C) stretches out the lesion by tissue pressure. Larger balloons are capable of applying more pressure. Between about half an atmosphere and ten atmospheres may be necessary to dilate balloon 22' within the luminal surface 29. Before the balloon 22' is fully expanded, its pressure approximates the tissue pressure. However, once the balloon 22' cracks the plaque and is fully expanded, the outer layers of the tissue are somewhat elastic and the tissue pressure therefore no longer approximates the balloon pressure. The mild residual tissue pressure is helpful in applying the bioprotective material 26 to the arterial wall 28.

Referring again to FIG. 1C, the balloon section 22 having been placed adjacent to the plaque 14, is inflated to position 22', thereby opening the artery. At the same time, the fissures and dissected planes of tissue 24 are also opened.

After the catheter 20 is removed, following the teachings of conventional angioplasty procedures, the plaque 14 can collapse into the center of the artery, thereby resulting in an abrupt reclosure of the artery and the possibility of an acute myocardial infarction.

Figure 1C:
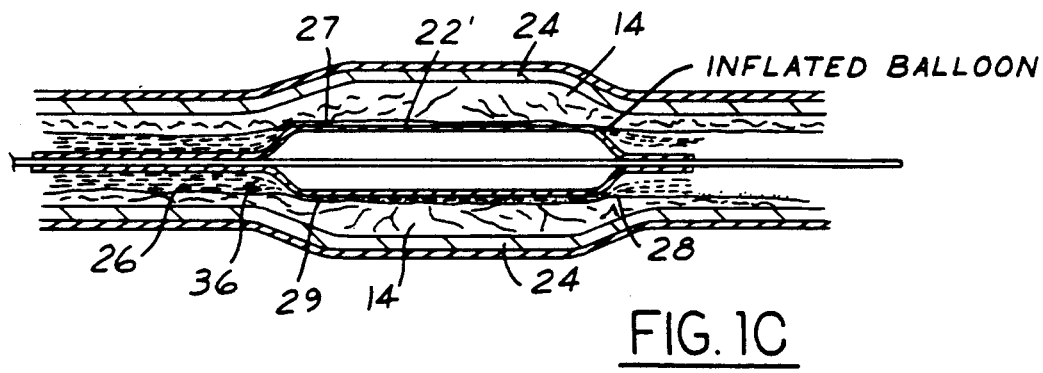
FIG. 1C is a cross-sectional view of the procedure disclosed by the present invention, in which the balloon is inflated and the bioprotective material is entrapped between the balloon and the arterial wall, the bioprotective material also entering vessels of the arterial wall and fissures which result from previously administered angioplasty procedure.

Following prior art techniques, even less severe disruptions in the arterial wall commonly result in gradual restenosis within three to six months after conventional balloon angioplasty. This occurs in part because platelets adhere to exposed arterial tissue surfaces. FIG. 1C is helpful in illustrating the fissures or dissected planes of tissue 24 which result from conventional angioplasty procedures. The presence of regions of blood flow separation and turbulence within the arterial lumen 36 predispose to microthrombi deposition and cellular proliferation within the arterial wall 28.

To overcome these and other problems resulting from prior art approaches, the method of the present invention applies the bioprotective material 26 to a lesion 27 of the luminal surface 29 of the arterial wall 28 and to deeper surfaces lining fissures and vessels of the arterial wall. The angioplasty catheter 20 is first positioned adjacent to the lesion 27 being treated. Next, the bioprotective material 26 is delivered between the arterial wall 28 and the angioplasty catheter 20. Before completing inflation of the balloon, the bioprotective material 26 lies within fissures and vessels of the arterial wall and between the arterial wall 28 and the angioplasty catheter 20, and downstream thereof. During apposition of the angioplasty catheter 20 to the arterial wall 28, a layer of the bioprotective material 28 is entrapped therebetween. Because of capillary action and pressure exerted radially outwardly by the balloon, the bioprotective material 26 further enters and permeates the vessels of the arterial wall as well as the fissures and dissected planes of tissue 24. As a result, localized delivery of the bioprotective material 26 is made possible.

Turning now to FIG. 2, it may be seen that thermal energy generated from an optical diffusing tip 32 is represented schematically by radially emanating wavy lines. The thermal energy bonds the bioprotective material 26 to the arterial wall 28 and within the tissues 24.

The guide wire 10 may be replaced with an optical fiber 30 having an optical diffusion area or tip 32 located within the inflated balloon 22'. The catheter 20 is inserted around the optical fiber in lumen 36. Expansion of the balloon 22 is produced by a transparent fluid through inflation port 38 in termination apparatus generally located at 40. The fluid utilized for inflation of the balloon may be a contrast medium or crystalloids, such as normal saline, or five percent dextrose in water. Each is relatively transparent to such thermal energy as radiation. After passing through the catheter wall 42, the fluid continues through a channel 44 in the outer catheter sheath, thereby inflating the balloon 34. After inflation, for example, laser radiation 46 is introduced into the optical fiber 30 for transmission to the optical diffusion tip 32. The laser radiation is then diffused therefrom and impinges upon the bioprotective material 26 and the arterial wall 28 after fracture or dissection of the plaque 14 has occurred following prior angioplasty. It will be apparent that there exist a variety of ways to deliver thermal energy to the area to be treated. Microwave, radio-frequency, or electrical heating of the fluid each are possible techniques.

The invention disclosed contemplates injection of the bioprotective material 26 through the guiding catheter 20, the tip of which lies near the origin of, for example, a coronary artery before passage of a small balloon catheter through an inner channel of the guiding catheter. The bioprotective material may be injected through the guiding catheter along with flowing blood. Alternatively, the physician may use a small tube that fits over the shaft of the balloon catheter 20 and inject drugs proximal to or upstream from the balloon's location. If the physician wishes, a separate channel within the angioplasty catheter could be used to inject the bioprotective material through exit holes located in the shaft of the catheter, proximal to the balloon.

In practicing the invention, the guide wire 10 may extend through a central channel in the balloon and extend down the arterial lesion path. Alternatively, the guide wire 10 can be fixed to a central channel in the balloon or be freely movable with respect thereto.

Unlike conventional approaches which may require repeated application of the angioplasty procedure with intermittent inflation of the balloon to avoid prolonged interruption of blood flow, the procedure taught by the present invention does not require multiple inflations, and is applied only once for about a twenty second period of thermal treatment followed by about a twenty second period of cooling before balloon deflation. If thicker layers of bioprotective material 26 are required, then the disclosed technique can be used repeatedly.

Figure 3:
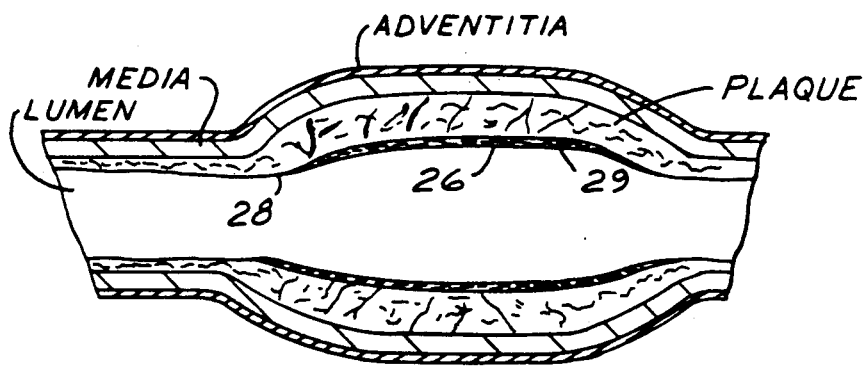
FIG. 3 is a cross-sectional view of the result of utilizing the procedure of the present invention, illustrating a smooth channel formed by the insoluble layer of bioprotective material at the luminal surface and within sealed fissures and sealed vessels of the arterial wall, thereby providing at least semipermanent protection to the arterial wall, despite contact with blood flowing adjacent thereto.

Referring now to FIG. 3, after removing the angioplasty catheter 20, the bioprotective material 26 remains adherent to the arterial wall 28. As a result, the luminal surface 29, fissured tissues, and vessels of the arterial wall are coated with an insoluble layer of the bioprotective material 26. The insoluble layer provides at least semi-permanent protection to the arterial wall 28, despite contact with blood flowing adjacent thereto.

It will be appreciated that until the invention disclosed herein, there existed no technique for coating the luminal surface and deeper tissue layers of arteries with a bioprotective material after injury sustained in conventional angioplasty. Although balloons can be used to deliver stents which act as scaffolding devices, the struts of the stents generally are inherently thrombogenic as a result of disruption of laminar flow adjacent to each stent and at the axial ends thereof. Continuous, smooth-walled stents can be fabricated, but use of such stents could result in occlusion of large side branches which are invariably present in coronary arteries. In addition, stents may elicit a foreign body inflammatory reaction, are technically difficult to place, and are relatively unforgiving if placed inappropriately.

As a result of the contribution made by the present invention, it is now possible to coat the luminal surface and deeper layers of injured arteries with insoluble, and therefore permanent or semipermanent bioprotective materials. One or more of such bioprotective materials could, depending upon the physician's preference, be pharmacologically active. Thrombogenic, inflammatory, or proliferative adverse reactions, or other adverse reactions which normally occur after angioplasty may therefore be reduced. As a result, both short and long term luminal results are improved.

In a preferred method of practicing the present invention, thermal energy is applied to the lesion to bond the bioprotective material 26 to the arterial wall using laser balloon angioplasty (LBA). In this procedure, heat (including heat emanating from nonlaser energy sources) and pressure are applied simultaneously to remodel the arterial lumen. The protective biocompatible layer 26 can then be applied to the luminal surface and deeper layers of the arterial wall in ways which are not possible with any other type of angioplasty procedure. Following the teachings of the present invention, drugs may now be incorporated into the biocompatible layer to mitigate any adverse biologic responses of the arterial wall to mechanical or thermal injury.

One method of applying the biocompatible layer to the luminal surface contemplates injecting a solution or fine dispersion of one or a combination of materials into the artery during balloon inflation. At least one component of the materials becomes bonded to the luminal surface by undergoing a physical change such as a phase transition, transient breakage of non-covalent bonds with subsequent cross-linkage with both itself and the arterial wall upon cooling, or by a chemical reaction, such as polymerization. The coating of bioprotective material thereby provided is a relatively water-insoluble layer which is bonded to tissues at the luminal surface.

This layer will persist chronically, despite contact with flowing blood, unlike a water-soluble material.

A preferred technique calls for the use of albumin in solution, which is trapped between the balloon 22 and luminal surface 29 during balloon inflation. The albumin precipitates onto and is bonded to the luminal surface 29 and deeper layers of the arterial wall as a result of thermal denaturation. It will be appreciated that other types of potentially injectable, heat-transformable materials may be used. Such materials include high molecular carbohydrates such as starch and dextran, liposomes, platelets, red blood cells, fibrinogen, and collagen.

Chemically or thermally cross-linked albumin has been used by others to coat surfaces of prosthetic vascular grafts in order to provide a non-thrombogenic layer. Since a precipitated layer of albumin is insoluble, it may persist on the luminal surface for at least four weeks before the layer of albumin disappears. By that time, the surface may be completely healed with a new confluent layer of ingrowing endothelial cells, which typically takes about two weeks.

It is also possible to apply directly to the arterial wall one or more of a wide variety of therapeutically useful pharmaceutical agents coupled to the albumin, thus providing local drug therapy to prevent restenosis of the angioplastied lesion. Examples of such drugs include anticoagulants (e.g. heparin, hirudin, anti-platelet agents, and equivalents), fibrinolytic and thrombolytic agents, anti-inflammatory agents (e.g. steroidal and nonsteroidal compounds), and anti-proliferative compounds (e.g. suramin, monoclonal antibodies to growth factors, and equivalents). Drugs may be bound covalently to albumin in solution, prior to injection, so the drug will be permanently fixed to the heat-precipitated layer of albumin.

Also considered within the scope of the present invention is the use of a drug which is physically and/or chemically trapped within or by the precipitated layer of albumin. Microspheres could be fabricated in vitro to trap virtually any type of drug therewithin prior to injection into the lumen of the artery. In such an environment, the rate of diffusion of the drug through the walls of the microspheres could be adjusted by the degree of albumin cross-linking induced thermally or chemically. With a currently well-developed technology of fabrication of albumin microspheres, the half life for diffusion of entrapped drugs from the microspheres can be varied from minutes to many months. The dimensions of the microspheres can be made to be smaller than 3 microns, thereby avoiding the problem of capillary plugging. When the drug-containing albumin microspheres are injected into the artery, with or without albumin in solution, thermal cross-linking during thermal exposure will induce adherence of the microspheres to the arterial wall.

Similar concepts could also be applied to a wide variety of other types of microencapsulated drug preparations. The encapsulating medium may consist of liposomes, both high and low molecular weight carbohydrates, sulfated polysaccharides, platelets, red blood cells, gelatin, fibrin, inorganic salts, phosphate glasses, and synthetic polymeric materials. Examples of synthetic polymeric materials include glycolide, lactide, silicone, polyvinylpyrrolidone, poly (methyl methacrylate), and polyamide polymers; ethylene-vinyl acetate copolymer; polyesters such as polyglactin, vicryl, Dexon, and polydioxanone polymers; and hydrogels, such as poly (hydroxyethyl methacrylate), polyacrylamide, polyvinyl alcohol, and gamma-irradiated polyelectrolytes. Additionally, endogenous platelets, removed from the same patient to be treated, can be made to incorporate virtually any water-soluble drug. It should be noted that thermal denaturation of proteins on the surface of a platelet during application of this blood element to the arterial wall can be expected to prevent the platelet from functioning normally as an initiator or promotor of thrombus formation.

Microspheres of any material, when injected along with an albumin solution, would be similarly trapped with heat-induced precipitation and crosslinking of the albumin. Alternatively, the microcapsules could be thermally bonded directly to tissues, without the use of any additional crosslinkable material. Microcapsules could also be formed in situ at the balloon-tissue interface as a result of heating the bioprotective material in solution. A water soluble drug which is injected simultaneously with the bioprotective material in solution would thereby become encapsulated upon thermal treatment.

Both water soluble and water-insoluble drugs may be encapsulated within the microspheres. In addition to anti-coagulants, thrombolytic, fibrinolytic, anti-inflammatory, or anti-proliferative agents, other potentially useful drugs or materials may be encapsulated. Examples include immunosuppressant agents (cyclosporin; alkylating agents; adriamycin; and equivalents), glycosaminoglycans (heparan sulfate; dermatan sulfate and equivalents), collagen inhibitors (colchicine; D-penicillamine; 1, 10 phenanthroline, and equivalents), and endothelial cell growth promotors. In addition, a chromophore may be encapsulated in order to enhance absorption of electromagnetic radiation.

Alternatively, a photosensitive drug such as a porphyrin may be encapsulated in order to enhance photodynamic therapy of tissues within which the microcapsules are thermally bonded. When a chromophore is encapsulated at the surface of microcapsules, the use of pulsed electromagnetic radiation, the wavelength of which matches the absorption spectrum of the chromophore, could be used to selectively and briefly heat only the surface of each microcapsule to bond the microcapsules to the luminal surface, without damaging thermally labile materials encapsulated within the interior of the microcapsules. It will be apparent to those of ordinary skill that many variations of the concept are possible.

As discussed earlier, in addition to the pharmacologic benefit of the invention, cracks and recesses within the mechanically injured arterial wall are filled in with the insoluble material, thereby producing a smoother and, hence, less thrombogenic luminal surface.

A further benefit of the invention results from the small vessels within the plaque and normal arterial wall (vasa vasorum) being filled with the material delivered during balloon inflation. Thermal cross-linking of at least one of the materials, such as albumin, effectively bonds the materials to the luminal surface of the small vessels. In addition, the material fills and become bonded to tissues lining fissures and dissections. Drugs are therefore delivered throughout the full thickness of the plaque and arterial wall. Moreover, the bioprotective material, when trapped between dissected tissues, could additionally be used to enhance thermal fusion thereof. A level of coagulation or precipitation achieved by thermal exposure alone is generally insufficient to obliterate side branches larger than about 0.5 mm because the radially directed pressure applied by the inflated balloon does not bring opposing walls of the lumen of a side branch firmly together, a necessary condition for thermal closure of such arteries.

Obliteration of the lumina of small vessels of the arterial wall is achievable by thermally coagulating a sufficient amount of albumin within the lumina or by thermally bond opposing walls of the small vessels which are coated by pressure. As a result, the entire balloon-dilated arterial segment would be rendered relatively impermeable to blood and blood-born components. For example, infiltration of leukocytes into the plaque and arterial wall is greatly slowed, and permeation of growth factors and of mediators of inflammation is impeded. Likewise, the thermally treated arterial wall provides a semi-permanent depot for entrapped drugs, the diffusion of which is slowed by the relatively impermeable nature of the arterial wall.

Disclosure of the invention thus far has contemplated the injection of bioprotective material 26 between the inflating balloon and the arterial wall. Another method of administering the bioprotective material 26 contemplates applying a thin sleeve of such material to the external surface of the LBA balloon. The thin sleeve is then transferred to the luminal surface as a result of heat and pressure. Prior to heating, one or more components of the bioprotective material may be either soluble or insoluble in water. If the component is soluble, it would be covered with a thermally labile, insoluble layer, or it could be micro encapsulated in a water insoluble, thermally labile medium. Thermal coagulation of one or more of the components of the material on the balloon would result in transfer of the balloon coating material to the luminal surface, to which it will be persistently affixed. Before transfer of the bioprotective material 26 from the balloon 22, the material could be either weakly or strongly adherent to the balloon surface. If strongly adherent, heat would destroy the adhesion between the balloon surface and the materials. This approach avoids the injection of bioprotective material 26 into the bloodstream. After the balloon is deflated, it is likely to have a temperature between 50° C. and 70° C. At this time, the temperature of the tissue is well above normal. Accordingly, a preferred approach is to attach the bioprotective material to the balloon with a biocompatible adhesive which remains liquid at slightly elevated temperatures, thereby allowing the bioprotective material to become preferentially bonded to the tissue rather than to the balloon.

It will thus be apparent that the invention contemplates the application of a bioprotective layer 26 to the arterial wall 28, wherein the bioprotective layer 26 is pharmacologically active and delivers high concentrations of drugs locally, so that problems of systemic toxicity are circumvented. As the balloon 22 is inflated, bioprotective materials 26 are entrapped between the balloon surface and the surface of the tissue. Such material 26 is also entrapped within fracture planes deeper within the arterial wall and within the vasa vasorum. After full inflation of the balloon 22' and physical entrapment within the arterial interstices, thermal energy is applied to the entire wall or selectively to the bioprotective material, if there is provided a strongly absorbing chromophore therewithin which absorbs laser energy preferentially.

The invention may be practiced by applying laser energy to heat the entire arterial wall 28 or the luminal surface alone to an elevated level above body temperature, preferably to 100° C. or less for a duration typically between about 15 and 60 seconds and most preferably between 15 and 30 seconds. The laser energy emanates from the interior of the balloon in a generally cylindrical pattern of light. Typically about five seconds are needed to reach the desired temperature. The optimal duration at the elevated level is probably between about 10 and 60 seconds. More energy is administered initially, typically for about 5 seconds, to rapidly raise the tissue temperature up to a target level. The delivered energy is then diminished so that the target temperature may be maintained. As the tissue is cooled by terminating laser exposure, the bioprotective material, such as albumin or starch, is bonded to the tissue.

Another technique of administering the bioprotective material is to use a perforated balloon which has tiny apertures therein and which allows the injection of bioprotective materials into the arterial wall. Such materials may then be injected under pressure through the balloon material. They must ordinarily be water-soluble or, in the case of microspheres, non-aggregating, in order to avoid obstruction of capillaries in the likely event that the material will enter the general circulation through side branches adjacent to the balloons. One problem with the use of water soluble materials and non-aggregating microspheres is that the materials or microspheres will be washed away quickly from the arterial wall. However, by heating the material after injection, and heating only the material that is trapped in the wall, it is not free to embolize downstream and obstruct anything else. In addition, when heat is applied to render the material both adherent and water-insoluble or, in the case or microspheres, to induce adherence of the insoluble microspheres, the material will stay more permanently within the tissue. Although the use of thermal energy to bond bioprotective materials to the arterial wall is the preferred method, it is apparent that application of pressure alone by the angioplasty catheter could be used to rupture pressure-sensitive microcapsules, thereby releasing bioprotective materials and physiologic adhesives which would bond the bioprotective materials to tissue.

Reference was made earlier to the use of microspheres containing the drug to be administered. Factors which influence speed of distribution of drug from a microsphere include the degree of albumin cross-linkage, for example, the size of the encapsulated molecules, and the size of the microspheres. Such factors can be varied in order to produce fast or slow diffusion rates. The drug emanating from such microspheres may be entrapped not only at the luminal surface where the effect of the drug is governed by the diffusion rate. But the microspheres may also be entrapped within the deep interior of cracks and the vascularity of the vasa vasorum. Such cracks will be obliterated by thermal treatment, so that the entire crack no longer will have vascular access to the general blood circulation and minimal material will be irrigated away.

As a result of practicing the invention, there results a wide open, smooth channel because of thermal remodeling and bonding of the bioprotective material 26 to the lesion 27. Thermal energy dries up any clot, and produces a favorable luminal result. In addition, there remains a coating of drug in a bioprotective layer because a water-insoluble layer, such as albumin or starch, is bonded to the arterial wall. Enclosed therewithin may be microcapsules containing a pharmacologically active drug disposed along the luminal surface as well as within the deeper layers of the wall.

As another example of practicing the technique disclosed, there will now be described a recently conducted animal study. Dogs were first given a suitable dosage of pentobarbital. Selected arteries were injured. Albumin microcapsules which entrapped both heparin and a fluorescent dye were fabricated and injected intraluminally into the injured arteries bilaterally in three animals. Balloon pressure was applied without heat to ipsilateral arteries, and LBA was applied to contralateral arteries. Blood flow was restored for one hour in one animal and for four hours in another. These animals were sacrificed after the period of blood flow restoration. The third animal was sacrificed acutely in order to provide a baseline for comparing the density and quantity of bioprotective material remaining adherent to the luminal sacrifice after blood flow restoration. It was found that without heat, there was minimal evidence of adherence of the fluorescent dye. At the contralateral sites, as a result of the laser exposure, fluorescent granules of the microcapsules were apparent and still present at the luminal surface. By fluorescence microscopy, no loss of bioprotective material was noted in arteries perfused for one and four hours, compared to the arteries of the animal sacrificed acutely.

In another example of the invention disclosed, microspheres of albumin were prepared with standard techniques using an oil/water interface and sonicating an albumin solution in an organic material such as cottonseed oil. The albumin in the microspheres ranged in size from less than a micron up to $40 \geq 50$ microns. Such microspheres can easily be made, if required, to be uniform in size and be less than a micron in diameter. A suspension of microspheres in physiologic saline was then applied onto the luminal surface of pig aortas in vitro. Albumin was identifiable by the presence of a fluorescent dye incorporated therewithin. When the albumin microspheres were exposed to ultraviolet light, the dye fluoresced red. The bioprotective material was then applied to the tissue surface and covered with a sheet of polyethylene terephthalate (PET), a highly cross-linked form of polyethylene used for the LBA balloon. Then, a transparent glass slide was applied above the PET material and the combination was subjected to pressure. Excess fluid was expressed away from the surface. While pressure was applied, the surface was exposed to about 70 watts continuous wave Nd:YAG laser radiation for about twenty to thirty seconds over a surface area of approximately 2 square centimeters. All tissue sections were then vigorously washed in saline warmed to body temperature.

About a dozen treatment sections were examined. Absent laser exposure, all control segments showed no adherence of the microspheres to the surface. All the laser-exposed surfaces, however, showed albumin in several different ways. A pale red color of the dye in the albumin was readily apparent both to the naked eye and with the aid of a microscope. Additionally, fluorescent microscopy confirmed the presence of albumin in frozen sections of the tissue. Further, clumps of microsphere granules were prominent in the crevices of the tissue. The frozen sections studied revealed a satisfactory layer of the bioprotective material at the luminal surface. Stereomicroscopy confirmed that the crevices were filled by coagulated microspheres. By filling in such crevices with coagulated materials, a smoother luminal surface resulted, which produces less turbulent flow patterns and thus less tendency for clots to form.

In a separate in vitro study, a solution of hydroxyethyl starch, a potentially clinically useful volume expander, was applied to about a dozen pig and human atheromatous aortic tissue sections. Laser exposure was performed in a manner similar to that described for the albumin microsphere study. After washing the tissue sections in normal saline, control sections not exposed to laser radiation showed no adherence of the starch, while all laser-exposed sections showed significant adherence. Light microscopy showed a uniform layer of precipitated starch granules, approximately 2 microns in size, on the luminal surface, and all laser-exposed sections demonstrated a characteristic blue color when iodine, added to the luminal surface, reacted with the precipitated, adherent starch.

Although conventional balloon angioplasty is by far the commonest angioplasty procedure which injures the arterial wall, virtually every other angioplasty procedure currently practiced or under experimental development also results in injury to the arterial wall. Examples of alternative angioplasty techniques include mechanical, laser-based, and ultrasonic atherectomy procedures as well as use of stents. In each case, the present invention could be used to apply bioprotective materials after angioplasty injury in order to reduce the incidence of lesion recurrence. Moreover, angioplasty catheters other than balloon catheters could be used to deliver thermal energy. For example, a metal probe, positioned adjacent to the lesion to be treated, could be heated with laser, electrical resistive, radio-frequency, or microwave energy, and the bioprotective material could be heated by thermal conduction from the probe.

While the preferred method of applying thermal energy is the use of electromagnetic radiation, including laser, electrical resistive, radio-frequency, and microwave energy sources, alternative methods may be used. Such methods include chemical and ultrasonic techniques. Moreover, externally focussed energy sources directed inwardly, including ultrasonic and microwave energy, could alternatively be used to heat the balloon, arterial wall, or bioprotective material without the use of an energy-delivering catheter.

There has been provided in accordance with the invention a method for applying bioprotective materials to the luminal surface and arterial wall during balloon angioplasty which addresses the needs and solves the problems remaining from conventional approaches. While the invention has been described in conjunction with specific modes for practicing the invention, it is evident that many alternatives, modifications, and variations will be apparent to those skilled in the art in light of the foregoing description. Accordingly, it is intended to embrace all such alternatives, modifications, and variations as fall within the spirit and broad scope of the following claims.

What is claimed is:

1. A method for treating a lesion in an arterial wall having plaque thereon and a luminal surface, the arterial wall having been injured during an angioplasty procedure, the arterial wall and the plaque including fissures resulting therefrom, the method comprising the steps of:

positioning an angioplasty catheter adjacent to the lesion being treated;

delivering a bioprotective material between the arterial wall and the angioplasty catheter so that the bioprotective material is entrapped therebetween and permeates into the fissures and vessels of the arterial wall during apposition of the angioplasty catheter thereto;

applying thermal energy to the lesion, thereby bonding the bioprotective material to the arterial wall and within the fissures and vessels of the arterial wall; and removing the angioplasty catheter, the bioprotective material remaining adherent to the arterial wall and within the fissures and vessels thereof, thereby coating the luminal surface with an insoluble layer of the bioprotective material so that the insoluble layer provides at least semi-permanent protection to the arterial wall, despite contact with blood flowing adjacent thereto.

2. The method of claim wherein the angioplasty catheter utilized includes an inflatable balloon.

3. The method of claim 2 wherein the inflatable balloon is at least partially inflated before delivering the bioprotective material between the arterial wall and the inflatable balloon so that the layer of the bioprotective material may be formed therebetween.

4. The method of claim 1 wherein the bioprotective material utilized is macroaggregated albumin which bonds to the luminal surface and within fissures and vessels of the aterial wall as a result of the application of thermal energy.

5. The method of claim 1 wherein the bioprotective material utilized comprises platelets, injected as a suspension, which upon being trapped between the inflatable balloon and the luminal surface become adherent to the luminal surface and to tissues adjacent to fissures and vessels of the arterial wall as a result of the application of thermal energy.

6. The method of claim 1 wherein the bioprotective material comprises red blood cells, injected as a suspension, which upon being trapped between the inflatable balloon and the luminal surface become adherent to the luminal surface and to tissues adjacent to fissures and vessels of the arterial wall as a result of the application of thermal energy.

7. The method of claim 1 wherein the bioprotective material comprises liposomes, injected as a suspension, which upon being trapped between the inflatable balloon and the luminal surface become adherent to the luminal surface and to tissues adjacent to fissures and vessels of the arterial wall as a result of the application of thermal energy.

8. The method of claim 1 wherein the bioprotective material utilized is gelatin which upon being trapped between the inflatable balloon and the luminal surface bonds to the luminal surface and within fissures and vessels of the arterial wall as a result of the application of thermal energy.

9. The method of claim 1 wherein the bioprotective material utilized is a solution of fibrinogen which upon being trapped between the inflatable balloon and the luminal surface precipitates onto the luminal surface and within fissures and vessels of the arterial wall as a result of the application of thermal energy.

10. The method of claim 1 wherein the bioprotective material utilized is a solution of collagen which upon being trapped between the inflatable balloon and the luminal surface precipitates onto the luminal surface and within fissures and vessels of the arterial wall as a result of the application of thermal energy.

11. The method of claim 1 wherein the bioprotective material utilized is a solution of a high molecular carbohydrate which upon being trapped between the inflatable balloon and the luminal surface precipitates onto the luminal surface and within fissures and vessels of the arterial wall as a result of the application of thermal energy.

12. The method of claim 1 wherein the bioprotective material utilized entraps a useful pharmaceutical agent in order to provide local drug therapy directly to the luminal surface, and to deeper layers of the arterial wall.

13. The method of claim 12 wherein the useful pharmaceutical agent is an anti-coagulant.

14. The method of claim 12 wherein the useful pharmaceutical agent is a fibrinolytic agent.

15. The method of claim 12 wherein the useful pharmaceutical agent is a thrombolytic agent.

16. The method of claim 12 wherein the useful pharmaceutical agent is an anti-inflammatory agent.

17. The method of claim 12 wherein the useful pharmaceutical is an anti-proliferative compound.

18. The method of claim 12 wherein the useful pharmaceutical is an immunosuppressant.

19. The method of claim 12 wherein the useful pharmaceutical is a collagen inhibitor.

20. The method of claim 12 wherein the useful pharmaceutical is an endothelial cell growth promotor.

21. The method of claim 12 wherein the useful pharmaceutical is a sulfated polysaccharide.

22. The method of claim 1 wherein the bioprotective material includes a drug which is bound to albumin in solution prior to injection so that the drug is permanently affixed thereto by application of the thermal energy.

23. The method of claim 1 wherein the bioprotective material includes a drug which is physically trapped within a precipitated layer of albumin after the drug is injected with a solution of albumin.

24. The method of claim 1 wherein the bioprotective material comprises microspheres.

25. The method of claim 1 wherein the bioprotective material includes a drug preparation having an encapsulating medium.

26. The method of claim 25 wherein the encapsulating medium comprises albumin.

27. The method of claim 25 wherein the encapsulating medium comprises carbohydrates.

28. The method of claim 25 wherein the encapsulating medium comprises platelets.

29. The method of claim 25 wherein the encapsulating medium comprises liposomes.

30. The method of claim 25 wherein the encapsulating medium comprises red blood cells.

31. The method of claim 25 wherein the encapsulating medium comprises gelatin.

32. The method of claim 25 wherein the encapsulating medium comprises fibrin.

33. The method of claim 25 wherein the encapsulating medium comprises a synthetic polymer.

34. The method of claim 25 wherein the encapsulating medium comprises a sulfated polysaccharide.

35. The method of claim 25 wherein the encapsulating medium comprises an inorganic salt.

36. The method of claim 25 wherein the encapsulating medium comprises a phosphate glass.

37. The method of claim 1 wherein the bioprotective material is a suspension of microspheres in a physiologic solution.

38. The method of claim 1 wherein the step of removing the angioplasty catheter is followed by the step of bonding the bioprotective material to the lesion so that the bioprotective material remains adherent to the arterial wall, and fills cracks and recesses therewithin, thereby providing a smooth, luminal surface.

39. The method of claim 1 wherein the bioprotective material is delivered from a sleeve thereof provided upon the angioplasty catheter, the sleeve being disposed adjacent the arterial wall during apposition of the angioplastic catheter thereto, so that the sleeve of bioprotective material is transferred therefrom to the luminal surface, thereby becoming persistently affixed thereto upon applying the thermal energy and removing the angioplasty catheter.

40. The method of claim 1 wherein microspheres are formed in situ at the luminal surface and within the arterial wall as a result of the thermal energy applied to the bioprotective material.

41. The method of claim 1 wherein a drug, simultaneously injected with the bioprotective material, is entrapped within microspheres.

42. The method of claim 1 wherein the bioprotective material functions as a physiologic glue, thereby enhancing thermal fusion of fissured tissues within the arterial wall.

43. The method of claim 1 wherein the bioprotective material includes a chromophore which enhances absorption of electromagnetic radiation.

44. The method of claim 1 wherein a photosensitive dye is entrapped within the bioprotective material.

45. The method of claim 25 wherein the encapsulating medium comprises a chromophore which enhances absorption of electromagnetic radiation.

46. The method of claim 45 wherein the encapsulating medium entraps a photosensitive dye.

47. The method of claim 1 wherein the angioplasty catheter is a metal probe.

48. The method of claim 1 wherein the applied thermal energy is electromagnetic radiation.

49. The method of claim 48 wherein the applied thermal energy is continuous wave electromagnetic radiation.

50. The method of claim 48 wherein the applied thermal energy is pulsed electromagnetic radiation.

51. The method of claim 48 wherein the electromagnetic radiation is laser radiation.

52. The method of claim 48 wherein the electromagnetic radiation is radio-frequency radiation.

53. The method of claim 48 wherein the electromagnetic radiation is microwave radiation.

54. The method of claim 48 wherein the electromagnetic radiation is generated from electrical resistance.

55. The method of claim 1 wherein the bioprotective material is injected into the artery through the angioplasty catheter which is placed proximal to the lesion being treated.

56. The method of claim 2 wherein the bioprotective material is injected through a channel within the angioplasty catheter to the arterial wall by exiting through ports located proximal to the inflatable balloon.

57. The method of claim 2 wherein the bioprotective material is injected through the angioplasty catheter to the arterial wall through microscopic perforations provided within the inflatable balloon.

58. A method for treating a lesion in an arterial wall having plaque thereon and a luminal surface, the arterial wall having been injured during an angioplasty procedure, the arterial wall and the plaque including fissures resulting therefrom, the method comprising the steps of:
    positioning an angioplasty catheter adjacent to the lesion being treated;
    delivering a bioprotective material between the arterial wall and the angioplasty catheter so that the bioprotective material is entrapped therebetween and permeates into the fissures and vessels of the arterial wall during apposition of the angioplasty catheter thereto;
    applying thermal energy to the lesion, thereby bonding the bioprotective material to the arterial wall and within the fissures and vessels of the arterial wall; and
    removing the angioplasty catheter, the bioprotective material remaining adherent to the arterial wall and within the fissures and vessels thereof, thereby coating the luminal surface with an insoluble layer of the bioprotective material so that the insoluble layer provides at least semi-permanent protection to the arterial wall, despite contact with blood flowing adjacent thereto.

59. A method for treating a lesion in an arterial wall having plaque thereon and a luminal surface, the arterial wall and the plaque including fissures resulting therefrom, the method comprising the steps of:
    performing angioplasty;
    positioning an angioplasty catheter adjacent to the lesion being treated;
    delivering a bioprotective material between the arterial wall and the angioplasty catheter so that the bioprotective material is entrapped therebetween and permeates into the fissures and vessels of the arterial wall during apposition of the angioplasty catheter thereto;
    applying thermal energy to the lesion, thereby bonding the bioprotective material to the arterial wall and within the fissures and vessels of the arterial wall; and
    removing the angioplasty catheter, the bioprotective material remaining adherent to the arterial wall and within the fissures and vessels thereof, thereby coating the luminal surface with an insoluble layer of the bioprotective material so that the insoluble layer provides at least semi-permanent protection to the arterial wall, despite contact with blood flowing adjacent thereto.

60. The method of claim 1 wherein the step of applying thermal energy to the lesion comprises applying the thermal energy from the angioplasty catheter radially outwardly.

61. The method of claim 1 wherein the step of applying thermal energy to the lesion comprises delivering the thermal energy from a source thereof disposed outside the arterial wall radially inwardly.

62. The method of claim 1 wherein the step of applying thermal energy to the lesion comprises the step of applying thermal energy so that the temperature within the bioprotective material is raised to at least 50° C.

* * * * *